(12) United States Patent
Wen et al.

(10) Patent No.: US 10,849,874 B2
(45) Date of Patent: Dec. 1, 2020

(54) USE OF COMPOSITION FOR MODULATING ANGIOGENESIS

(71) Applicant: National Sun Yat-sen University, Kaohsiung (TW)

(72) Inventors: Zhi-Hong Wen, Kaohsiung (TW); Ping-Jyun Sung, Kaohsiung (TW); Han-Chun Hung, Kaohsiung (TW)

(73) Assignee: NATIONAL SUN YAT-SEN UNIVERSITY, Kaohsiung (TW)

( * ) Notice: Subject to any disclaimer, the term of this patent is extended or adjusted under 35 U.S.C. 154(b) by 110 days.

(21) Appl. No.: 14/958,940

(22) Filed: Dec. 4, 2015

(65) Prior Publication Data

US 2017/0157084 A1    Jun. 8, 2017

(51) Int. Cl.
| | | |
|---|---|---|
| A61K 31/343 | (2006.01) | |
| A61P 17/02 | (2006.01) | |
| A61K 35/614 | (2015.01) | |
| A61K 31/365 | (2006.01) | |

(52) U.S. Cl.
CPC .......... *A61K 31/343* (2013.01); *A61K 31/365* (2013.01); *A61K 35/614* (2013.01); *A61P 17/02* (2018.01)

(58) Field of Classification Search
CPC ........ A61P 17/04; A61P 17/02; A61K 31/365; A61K 31/343; A61K 35/614
See application file for complete search history.

(56) References Cited

U.S. PATENT DOCUMENTS

| | | | | |
|---|---|---|---|---|
| 8,246,969 | B2 * | 8/2012 | Engles | A61K 8/33 424/401 |
| 8,530,513 | B1 * | 9/2013 | Sheu | A61K 31/365 514/455 |

OTHER PUBLICATIONS

Nworu et al., "Extracts of Ficus exasperata leaf inhibit topical and systemic inflammation in rodents and suppress LPS-induced expression of mediators of inflammation in macrophages," J. Immunotoxicol. Jul.-Sep. 2013;10(3):302-10. PMID: 23098056. (Year: 2013).*
Andoh et al., "Nitric oxide enhances substance P-induced itch-associated responses in mice," Br. J. Pharmacol. Jan. 2003;138(1):202-8. PMID: 12522091. (Year: 2003).*
Orita et al., "Inducible nitric oxide synthase (iNOS) and alpha-melanocyte-stimulating hormones of iNOS origin play important roles in the allergic reactions of atopic dermatitis in mice," Exp. Dermatol. Nov. 2011;20(11):911-4. PMID: 21895774. (Year: 2011).*
Schwacha, "Macrophages and post-burn immune dysfunction," Burns 29(1):1-14 (2003). PMID: 12543039. (Year: 2003).*
Chang et al., "The optimal time for early burn wound excision to reduce pro-inflammatory cytokine production in a murine burn injury model," Burns. Nov. 2010;36(7):1059-66. PubMed 20471756. (Year: 2010).*
Agay et al., "Interleukin-6, TNF-alpha and interleukin-1 beta levels in blood and tissue in severely burned rats," Eur. Cytokine Netw. Mar. 2008;19(1):1-7. PMID: 18299267. (Year: 2008).*

(Continued)

*Primary Examiner* — Theodore R. Howell
(74) *Attorney, Agent, or Firm* — Hannah M. Tien

(57) ABSTRACT

The present invention relates to a method for modulating angiogenesis in a subject in need thereof, which comprises administering an effective amount of composition comprising excavatolide B and a pharmaceutically acceptable carrier to the subject.

2 Claims, 10 Drawing Sheets
(8 of 10 Drawing Sheet(s) Filed in Color)

(A)

(B)

(56) References Cited

OTHER PUBLICATIONS

Momohara S. et al., Analysis of perioperative clinical features and complications after orthopaedic surgery in rheumatoid arthritis patients treated with tocilizumab in a real-world setting: results from the multicentre TOcilizumab in Perioperative Period (TOPP) study, Mod Rheumatol (2013) 23:440-449 DOI 10.1007/s10165-012-0683-0.

Wang et al., The Interleukin-6 Cytokine System Regulates Epidermal Permeability Barrier Homeostasis, J Invest Dermatol 123:124-131, 2004.

Lin et al., Essential involvement of IL-6 in the skin wound-healing process as evidenced by delayed wound healing in IL-6-deficient mice, Journal of Leukocyte Biology, vol. 73, p. 713-721, Jun. 2003.

Barona J. et al., Optimal Support of Wound Healing: New Insights, Dermatology, Published online Jan. 17, 2020, DOI: 10.1159/000505291.

\* cited by examiner (A)

(B)

Control group    Atopic eczema group    EXC-B treating group

USE OF COMPOSITION FOR MODULATING ANGIOGENESIS

BACKGROUND OF THE INVENTION

Field of the Invention

The present invention relates to a method for modulating angiogenesis in a subject in need thereof, which comprises administering an effective amount of composition comprising excavatolide B and a pharmaceutically acceptable carrier to the subject.

Description of Prior Art

Angiogenesis is one common physiological process, which can be found in wound healing, female menstrual period and fetal growth. The vascular endothelial growth factor (VEGF) is identified as a primary stimulant affecting angiogenesis in a pathological condition.

The main reason that wound healing is difficult is that both diabetes mellitus and burn injury cause vascular atrophy or necrosis. Clinically, it is often found that such types of wounds are continuously accompanied with inflammatory reactions in addition to defective angiogenesis. However, drugs currently used for treating wounds do not specifically address the function of increasing angiogenesis.

Atopic eczema is an allergic skin disease which is a chronic, recurrent, itchy and abnormal skin condition related to gene and environment. The current clinical approach is to adopt a steroid treatment which has many serious side effects, such as skin dryness or albinism. Many studies have found abnormally increased angiogenesis in the skin suffered from atopic eczema while the expression level of pro-filaggrin is dramatically decreased. Many researches have demonstrated that the expression level of filaggrin in the skin is closely related to the maintenance of skin barrier function. If the expression level of filaggrin is dramatically decreased, it can cause damages to and dysfunction of the skin barrier. Moreover, it increases the probability of water loss via skin and infections caused by allergens.

Thus, the recovery mechanisms of many skin diseases (such as wounds and atopic eczema) are related to angiogenesis.

SUMMARY OF THE INVENTION

The present invention provides a method for modulating angiogenesis in a subject in need thereof, wherein the method comprises administering an effective amount of composition comprising excavatolide B and a pharmaceutically acceptable carrier to the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
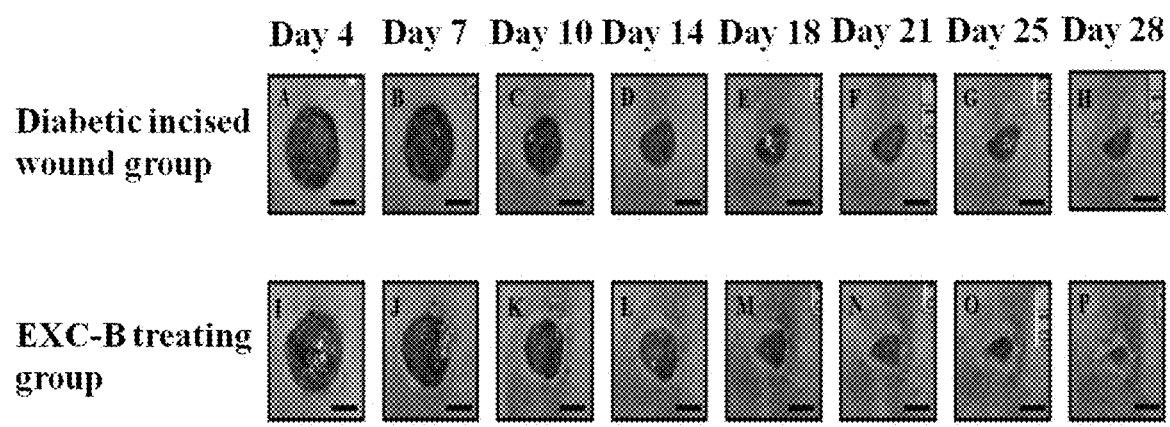
FIG. 1 shows the experimental result of the effect of excavatolide B (EXC-B) on the healing of a diabetic incised wound. (A)-(H) are results of the diabetic incised wound group (administered a normal lotion) and (I)-(P) are results of the EXC-B treating group (treated with 1 mg/0.2 ml of excavatolide B in a lotion). Scale bar=1 cm.

In the present invention, it demonstrates that excavatolide B (EXC-B) extracted from *Briareum excavatum* has a significant effect on accelerating wound healing of a patient suffered from diabetes mellitus or a chronic wound caused by burns. The main therapeutic mechanism of EXC-B is to promote angiogenesis and improve the condition of vascular atrophy and necrosis caused by a chronic wound by increasing the expression level of the vascular endothelial growth factor (VEGF).

In addition, the present invention also demonstrates that atopic eczema can cause an increased tissue secretion of the VEGF, but EXC-B can inhibit abnormal vascular proliferation caused by the VEGF. At the same time, EXC-B also can inhibit an itchy factor (such as substance P) and promote the secretion of a regulating factor for the skin barrier function (such as filaggrin) in order to improve an abnormal skin function caused by atopic eczema. Hence, the present invention demonstrates that EXC-B can treat atopic eczema and effectively improve the symptoms of atopic eczema.

Therefore, EXC-B has different mechanisms for the treatment of chronic wounds and atopic eczema. When the expression level of the VEGF in a tissue is decreased (e.g. vascular atrophy and necrosis), EXC-B will up-regulate the expression level of the VEGF; and when the expression level of the VEGF in the tissue is increased (e.g. an abnormally increased angiogenesis), EXC-B will down-regulate the expression level of the VEGF. Therefore, the present invention demonstrates that EXC-B can modulate the abnormal expression of the VEGF. It can be developed as a drug for modulating angiogenesis, which can be used for the treatment of abnormal angiogenesis-related diseases, particularly to improve skin conditions, such as chronic wounds or atopic eczema.

As used herein, "a" or "an" may mean one or more. As used herein in the claim(s), when used in conjunction with the word "comprising", the words "a" or "an" may mean one or more than one.

As used herein, the term "or" may mean "and/or."

The present invention provides a method for modulating angiogenesis in a subject in need thereof, wherein the method comprises administering an effective amount of a composition comprising excavatolide B (EXC-B) and a pharmaceutically acceptable carrier to the subject.

The excavatolide B of the present invention is extracted from *Briareum excavatum* and has a chemical structure formula as the following:

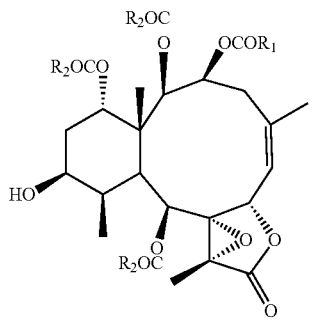

in which $R_1$ is $C_3H_7$; $R_2$ is $CH_3$.

Angiogenesis is the process of forming new blood vessels from existing blood vessels. It is a highly complex process involving extensive interplay between cells, soluble factors, and the extracellular matrix (ECM). As used herein, the term "modulating angiogenesis" comprises up-regulating and down-regulating the expression level of angiogenesis in order to improve symptoms. In one embodiment, the composition is administered locally or systemically by any means known to an ordinarily skilled artisan. In a preferred embodiment, the composition is administered via skin. In a more preferred embodiment, the composition is administered at least once daily.

In one embodiment, the pharmaceutically acceptable carrier comprises a dermatologically acceptable medium. The term "dermatologically acceptable medium" means a biologically appropriate substance, such as a salt, an ester or an amide. When this substance together with a selected effective composition is administered, it will not induce undesirable biological effects in the treated subject. In addition, this substance does not interact with any component in a pharmaceutical composition contained therein to generate a harmful substance. Likewise, as used herein, the term "dermatologically acceptable salt" or "dermatologically acceptable ester" means a biologically appropriate salt or ester.

In one embodiment, modulating angiogenesis is caused by modulating the expression level of the vascular endothelial growth factor (VEGF) in the subject. In a preferred embodiment, wherein modulating the expression level of the VEGF comprises up-regulating and down-regulating the expression level of the VEGF depended on a change of the expression level of the VEGF in the subject. In a more preferred embodiment, modulating the expression level of the VEGF comprises two conditions: (1) EXC-B up-regulates the expression level of the VEGF when the expression level of the VEGF is decreased in a tissue of the subject; and (2) EXC-B down-regulates the expression level of the VEGF when the expression level of the VEGF is increased in a tissue of the subject. Hence, EXC-B maintains a balance of the expression of angiogenesis.

In one embodiment, the subject is an animal. Preferably, the subject is a mammal. More preferably, the subject is a human.

As used herein, the "expression level" comprises the expression level of gene, RNA and protein.

The present invention adds an effective component into a suitable carrier for topical application by a technically well-known prescription for topical application. The selection of the carrier for topical application can provide a desirable type of carriers for the composition. In one embodiment, the formulation of the composition is selected from the group consisting of: a liquid form, a semi-solid form, a solid form and a spray form. In a preferred embodiment, the formulation of the composition is an ointment, a cream, a lotion, an emulsion, a microemulsion, a gel or a solution. In a more preferred embodiment, the formulation of the composition is the lotion or the gel. The selection of the above carriers must have no adverse effects to the effective component and other components in the composition for the topical application.

In one embodiment, the composition further treats an angiogenesis-related disease. In a preferred embodiment, the angiogenesis-related disease comprises a skin disease. In a more preferred embodiment, the skin disease comprises a wound and atopic eczema.

In another embodiment, the wound is a disease which decreases the expression level of the VEGF in the subject. Therefore, EXC-B can up-regulate the expression level of the VEGF of the wound to treat the wound. In a preferred embodiment, the wound comprises an acute wound and a chronic wound. In a more preferred embodiment, the wound comprises a chronic wound. Clinically, wounds are divided into acute wounds and chronic wounds based on the time required for healing and recovery. Acute wounds can be recovered during a series of orderly stages and in a relatively short period of time. A chronic wound is a very slowly recovered wound which requires a long period of time (e.g., longer than three months). The most common chronic wound comprises a venous ulcer, a diabetic ulcers and a pressure ulcer. In another embodiment, the chronic wound is a burn wound or a wound of a diabetic patient.

In one embodiment, the composition accelerates the wound healing of the skin. The wound was caused by a physical factor, a chemical factor, a mechanical factor, etc.; wherein these factors include but are not limited to trauma, burns, chemical burns, radiation injuries and physiological diseases.

In one embodiment, atopic eczema is a disease which increases the expression level of the VEGF in the subject. Therefore, EXC-B can down-regulate the expression level of the VEGF caused by atopic eczema to treat the symptoms of atopic eczema. In a preferred embodiment, the symptoms of atopic eczema comprise itchy skin and an abnormal skin barrier.

In one embodiment, the composition further treats itchy skin caused by atopic eczema. In a preferred embodiment, itchy skin of atopic eczema is caused by an itchy factor. In a more preferred embodiment, the itchy factor is substance P. Therefore, EXC-B treats itchy skin of atopic eczema by inhibiting the expression level of itchy factors (e.g. substance P).

In one embodiment, the composition further treats an abnormal skin barrier caused by atopic eczema. In a preferred embodiment, the composition treats an abnormal skin barrier caused by atopic eczema by increasing the regulating factor for the skin barrier function. The skin barrier disorder causes a generation of pores in the skin which in turn causes water loss via the skin and infections caused by allergens. Therefore, it will cause a dry skin, a cavity or a crazing condition. When severe condition occurs, it will cause diseases, such as atopic dermatitis, psoriasis, blistering diseases or allergic contact dermatitis. Therefore, the abnormal skin barrier caused by the atopic eczema decreases a moisturizer of a skin. In one embodiment, the abnormal skin barrier comprises a decreasing of a moisturizer of the skin. In a preferred embodiment, the composition has a function for increasing the moisturizer of the skin. In another embodiment, the regulating factor for the skin barrier function comprises pro-filaggrin and filaggrin. In a more embodiment, the regulating factor for the skin barrier function comprises filaggrin.

The term "treat" or "treating" in the present invention may comprise reversing, alleviating, ameliorating, relieving, delaying onset of, inhibiting progression of, reducing severity of, and/or reducing incidence of one or more symptoms or features of a disease and/or a condition induced by the disease.

In one embodiment, the effective amount of EXC-B in the composition is in a range of from about 5 µg/ml to about 2500 µg/ml. In a preferred embodiment, the effective amount of EXC-B in the composition is in a range of from about 25 µg/ml to about 500 µg/ml. In a more preferred embodiment, the effective amount of EXC-B in the composition is in a range of from about 50 µg/ml to about 250 µg/ml. The "effective amount" is an amount effective to prevent, lower, stop or reverse the development of, or to partially or totally alleviate existing symptoms of a particular condition for which the subject is being treated.

The present invention further relates to a cosmetics which comprises a topical pharmaceutical composition containing excavatolide B as described above.

The present invention also relates to a skin care product which comprises a topical pharmaceutical composition containing excavatolide B as described above.

The present invention also comprises a method for applying a topical pharmaceutical composition containing excavatolide B as described above on a skin.

EXAMPLES

The examples below are non-limiting and are merely representative of various aspects and features of the present invention.

1. Methods and Materials
(1) Preparation of Excavatolide B
Excavatolide B of the present invention is extracted from *Briareum excavatum* and has a chemical structure formula as the following:

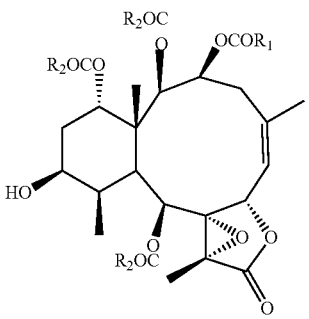

in which $R_1$ is $C_3H_7$; $R_2$ is $CH_3$.

(2) Treating Experiment of Diabetic Wound and Burn Wound (a) Preparation of Animal and Operation of Incised Wound in Diabetic Rat:

Male Wistar rats (400-450 g) were used in this experiment. The induction of diabetes was performed by using a citrate buffer solution to prepare streptozotocin (STZ, catalog No. 85882 FLUKA, Sigma, St. Louis, Mo., USA). The rats were anesthetized by 2.5% isoflurane and administered with STZ (60 mg/kg) by tail intravenous injection. A week after STZ injection, those rats with blood glucose levels more than 250 mg/dl were identified as successfully diabetic inducted rats. After the successfully induced rats were anesthetized by 2.5% isoflurane again, the present invention created an incision of full-layered skins by removing the skins of the selected incised location and range (a wound with 2 cm in diameter on the midline of the lumbar spine) on the back of the anesthetized rats. After the surgery of the incision of full-layered skins, the rats were randomly divided into two groups: (1) diabetic incised wound group (administered a normal lotion); and (2) EXC-B treating group (administered a lotion containing excavatolide B). The EXC-B treating group was treated with 1 mg/0.2 ml of excavatolide B in the lotion daily.

(b) Preparation of Animal and Operation of Burn Wound:

Male Wistar rats (400-450 g) were used in this experiment. After the rats were anesthetized by 2.5% isoflurane, the present invention selected four burned locations (two locations beneath the scapula of the rat and two locations in the midline of the lumbar spine) on the back of the anesthetized rat. The skins of the burned locations were tightened, and a copper block (2×2 cm) which was preheated to 175° C. by a dry bath was used to closely touch these skins of the locations for 10 seconds to form burn wounds of full-layered skins. The copper block was appropriately moved in order to form a quadrilateral form of burn wound during the burning process. Attention was paid not to add extra pressure on the copper block in order to ensure the same burn pressure each time during the burning process.

(c) Wound Observation and Area Calculation:

After being burned, the rats were anesthetized and then taken pictures according to experimentally designed dates. A series of pictures were taken by a digital camera (Coolpix P6000, Nikon, Japan) under the same condition (the diaphragm is 7.2, and the camera shutter is 1/60). A digital image capture system software (Diagnostic Instruments, Inc., Sterling Heights, Mich., U.S.A.) was used to analyze the captured wound pictures to calculate the wound area. The data of the wound area at each observation point were respectively presented at percentage of the wound area relative to day zero. At the same time, the weight of the rat was measured, and the rat was observed to find out any obvious strange appearance or behavior.

Pathologic Tissue Slice and HE Staining

After the rats had suffered injuries for specific days according to experimental design they were humanely sacrificed, PBS containing heparin (0.2 U/ml) at 4 degrees Celsius was injected into aorta until PBS carrying no color flowed out of the vein. 4% paraformaldehyde at 4° C. was injected to fasten it, the wounded area was carefully taken out by surgical blades and immersed into 10% Formalin fixing solution to be reserved at 4° C. and fixed for several days. Next, the fixed tissue was dehydrated and wax infiltrated. The skin tissue was dehydrated and wax infiltrated by utilizing a tissue automatic processing system. Afterwards, the tissue was embedded by a paraffin embedding machine into paraffin blocks. After tissue blocks were sliced through a paraffin microtome, tissue slices were stained by using hematoxylin and eosin stain. Upon completion, tissue slices were mounted by micro-mount, and completed sample slices then were placed on an optical microscope for observation, the sample slices were further photographed and recorded by the digital image capture system.

(3) Induced Atopic Eczema Model and Treatment Thereof (a) Preparation of Animal and Induction of Atopic Eczema:

The balb/c mice were used in this experiment. The method for inducing atopic eczema comprised: (1) prepared 1% DNCB in olive oil/acetone (1:4); and (2) applied 1% DNCB on the shaved skins of the backs of balb/c mice at day 1, 3, 9, and 11, respectively. The balb/c mice were randomly divided into three groups: (A) the control group; (B) the atopic eczema group; and (C) the EXC-B treating group. The EXC-B treating group was treated with excavatolide B for seven consecutive days starting from day 15. Next, the present invention assessed the treating effect of EXC-B on atopic eczema by image analysis of the appearance.

(b) Immunohistochemistry Staining:

Mice were scarified by cervical dislocation. The skin tissues of the backs of the mice were collected, fixed with formalin buffer and embedded in paraffin. The tissue sections were treated with a graded alcohol bath after the paraffin-embedded tissue sections (2 μm) were deparaffinized by xylene. Next, the sections reacted with 0.3% hydrogen peroxide for 30 minutes to remove endogenous peroxidase. After the paraffin-embedded tissue sections reacted with a protein K in a 4% phosphate buffer for 20 minutes at 37° C., the paraffin-embedded tissue sections were washed with 4% phosphate buffer and then blocked with horse serum diluted by phosphate buffer for 1 hr. Next, the sections were incubated with a diluted target protein antibody for 18-20 hr at 4° C. in a humid environment. After recycling the antibody, the horse serum was reused to incubate the sections for 1 hr and the sections subsequently reacted with an added corresponding secondary antibody for 90 minutes. After the sections reacted with ABC kit, DBA was used to produce color reaction, and the sections were air-dried with a graded alcohol bath and covered with a cover glass. The completed sample section was placed in an optical microscope (DM 6000, Leica Inc, Germany) and a stereomicroscope (APO Z16, Leica Inc. Singapore). The digital imaging output system of the microscope (idea SPOT, Diagnostic instruments Inc. USA) was used for taking pictures, recording the result of the sections and analyzing the sections.

(4) Data and Statistical Analysis

All data are shown as means±standard error of the mean (SEM). The data of the two groups were compared and statistically analyzed by using t-test. The differences between multiple groups were calculated by using one-way analysis of variance (ANOVA), followed by the Duncan test for comparison of multiple groups. The present invention defines statistical significance as $p<0.05$.

2. Test Results

Test of the Effect of EXC-B on the Healing of Diabetic Incised Wound

As shown in FIGS. 1, (A)-(H) were results of the diabetic incised wound group (administered a normal lotion), and (I)-(P) were results of the EXC-B treating group (treated with 1 mg/0.2 ml of excavatolide B in a lotion). In using image analysis, FIGS. 1 (A) and (I) showed the appearance at 4 days after incised injury; FIGS. 1 (B) and (J) showed the appearance at 7 days after incised injury; FIGS. 1 (C) and (K) showed the appearance at 10 days after incised injury; FIGS. 1 (D) and (L) showed the appearance at 14 days after incised injury; FIGS. 1 (E) and (M) showed the appearance at 18 days after incised injury; FIGS. 1 (F) and (N) showed the appearance at 21 days after incised injury; and FIGS. 1 (G) and (O) showed the appearance at 25 days after incised injury. The above results indicated that the EXC-B treating group which was administered with 1 mg/0.2 ml of excavatolide B in the lotion after incision the wound healing was significantly improved as compared to the diabetic incised wound group.

Figure 2:
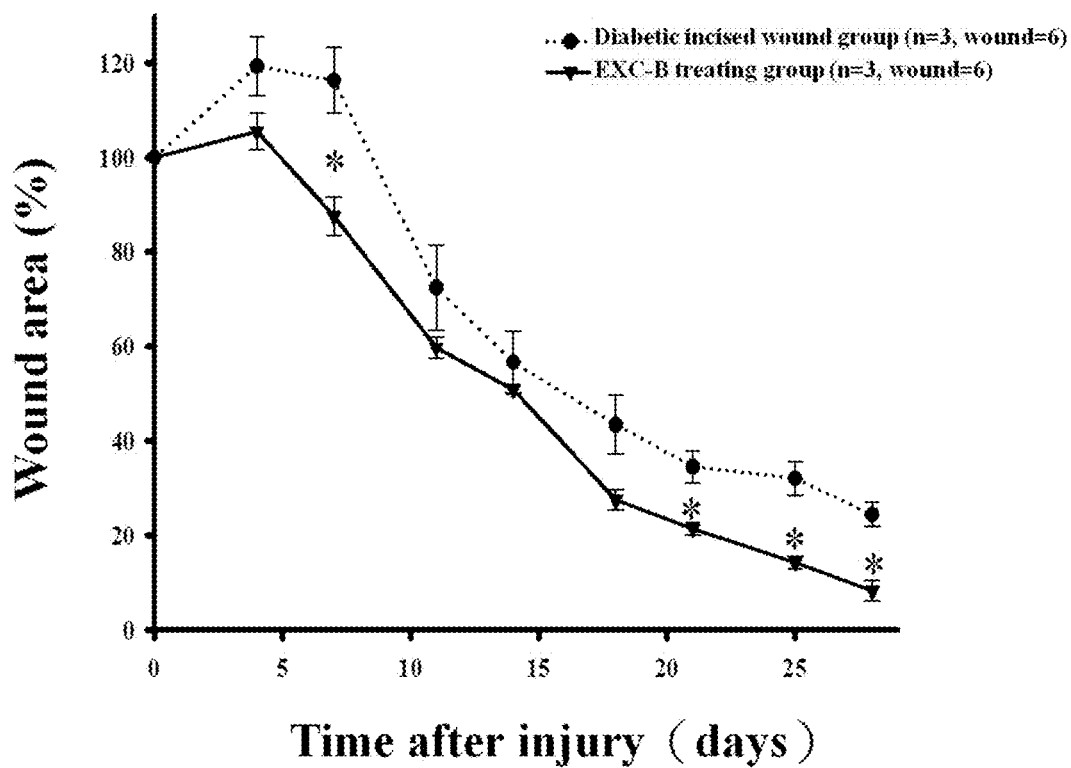
FIG. 2 shows the result of an assay of a wound area for quantifying the effect of excavatolide B (EXC-B) on the healing of a diabetic incised wound.

FIG. 2 showed a curve graph of the wound restoring area depended on time. The EXC-B treating group which was administered 1 mg/0.2 ml of excavatolide B in the lotion after incision the wound healing at day 7, 21, and 28 were significantly improved as compared to the diabetic incised wound group.

(2) Treating Test of EXC-B on Burn Wound

Figure 3:
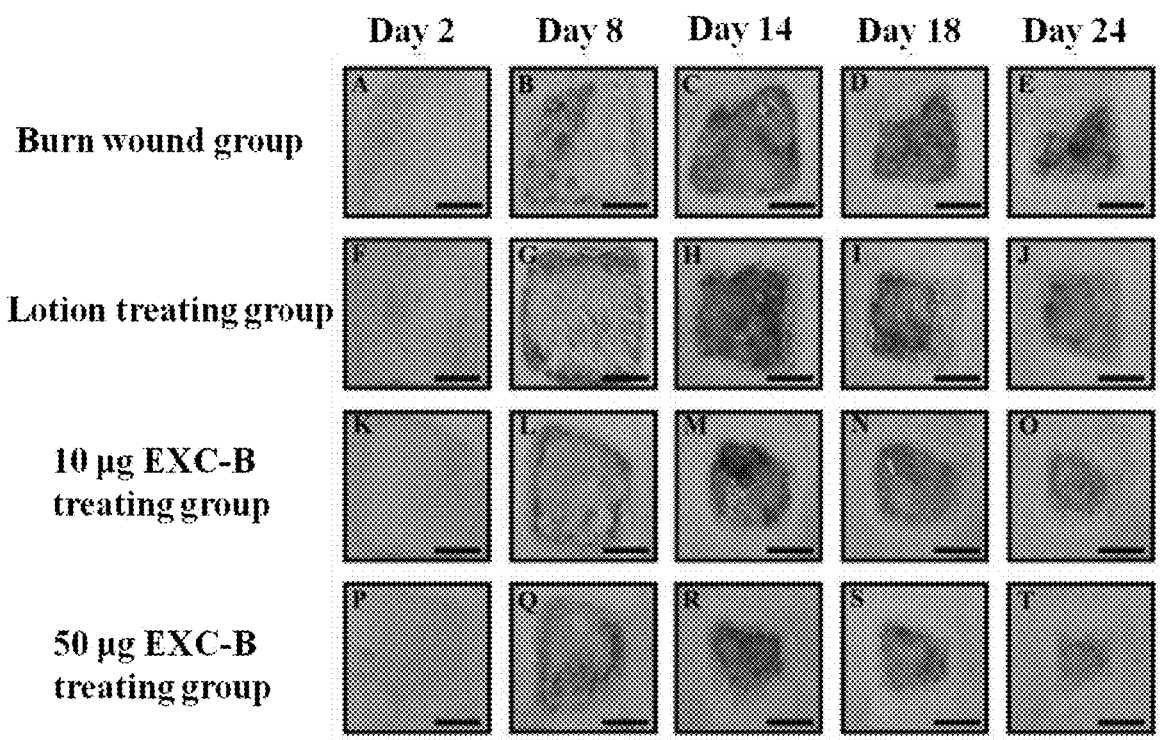
FIG. 3 shows the experimental result of the effect of excavatolide B (EXC-B) on the healing of a burn wound. (A)-(E) are results of the burn wound group (no treatment), (F)-(J) are results of the lotion treating group (administered a normal lotion), (K)-(O) are results of the 10 µg EXC-B treating group (treated with 10 mg/0.2 ml of excavatolide B in a lotion), and (P)-(T) are results of the 50 µg EXC-B treating group (treated with 50 mg/0.2 ml of excavatolide B in a lotion). Scale bar=1 cm.

As shown in FIG. 3, (A)-(E) were results of the burn wound group (no treatment); (F)-(J) were results of the lotion treating group (administered normal an lotion); (K)-(O) were results of the 10 μg EXC-B treating group (treated with 10 mg/0.2 ml of excavatolide B in a lotion); and (P)-(T) were results of the 50 μg EXC-B treating group (treated with 50 mg/0.2 ml of excavatolide B in a lotion). In using image analysis, FIGS. 3 (A), (F), (K) and (P) showed the appearance at 2 days after burn injury; FIGS. 3 (B), (G), (L) and (Q) showed the appearance at 8 days after burn injury; FIGS. 3 (C), (H), (M) and (R) showed the appearance at 14 days after burn injury; FIGS. 3 (D), (I), (N) and (S) showed the appearance at 18 days after burn injury; and FIGS. 3 (E), (J), (O) and (T) showed the appearance at 24 days after burn injury. According to the above results, the wound healing was significantly improved by administering 10 μg/0.2 ml (see FIGS. 3 (K) and (O)) or 50 μg/0.2 ml of EXC-B in the lotion (see FIGS. 3 (P) and (T)) after burn injury.

Figure 4:
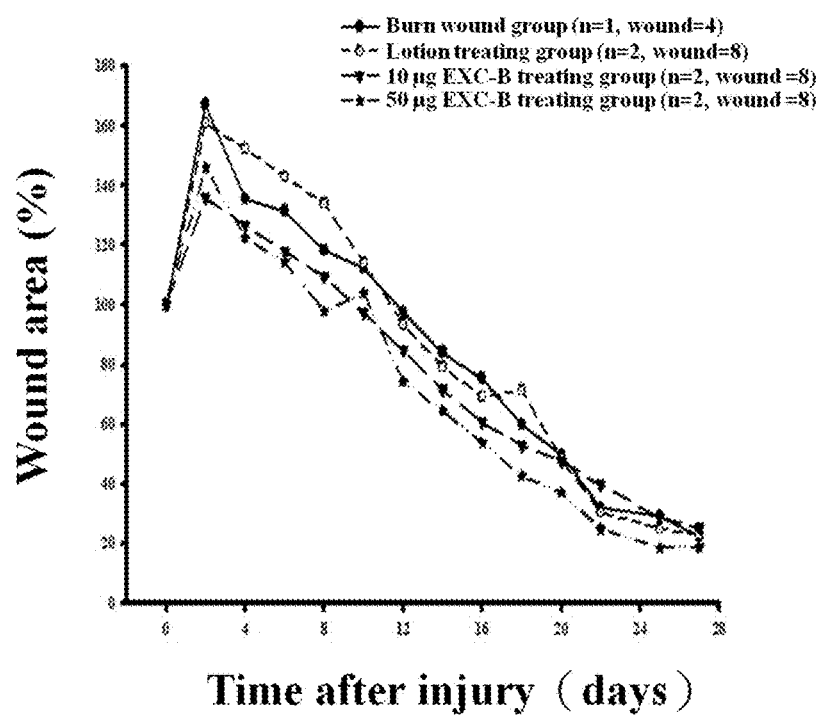
FIG. 4 shows a drawing of an assay of a wound area for quantifying the effect of excavatolide B (EXC-B) on the healing of a burn wound. (A) is a curve graph of a burned restoring area depended on time and (B) is an analysis graph of the area under the curve (the healing area of each group=the area under the curve of each group during day 0-27—the area under the curve the burn wound group during day 0-27).
Figure 4:
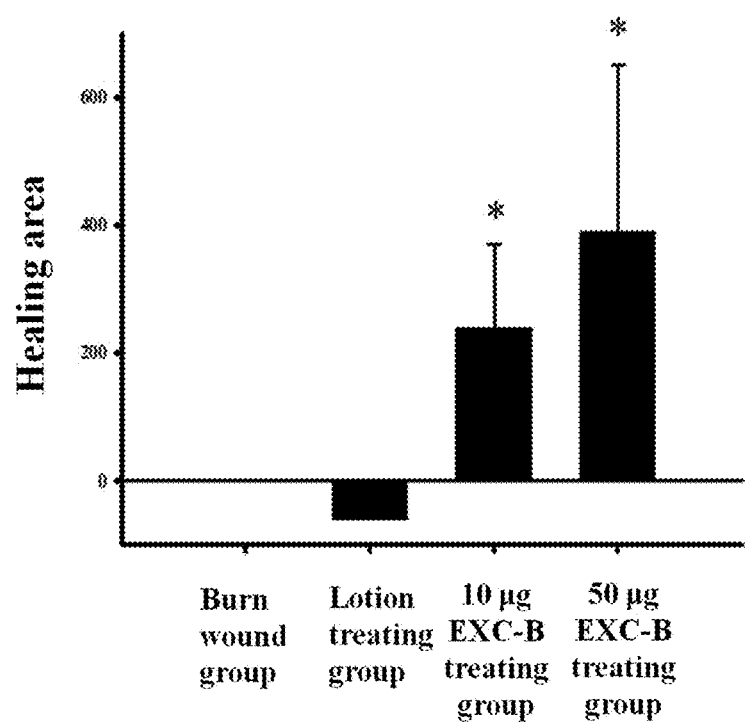

FIG. 4 showed a drawing of an assay of a wound area quantifying the effect of excavatolide B (EXC-B) on the healing of a burn wound, in which (A) showed a curve graph of a burned restoring area depended on time and (B) showed an analysis graph of the area under the curve. According to the results of FIG. 4, the 10 μg EXC-B treating group and 50 μg EXC-B treating group could significantly accelerate wound healing depended on time as compared to the burn wound group and the lotion treating group.

Figure 5:
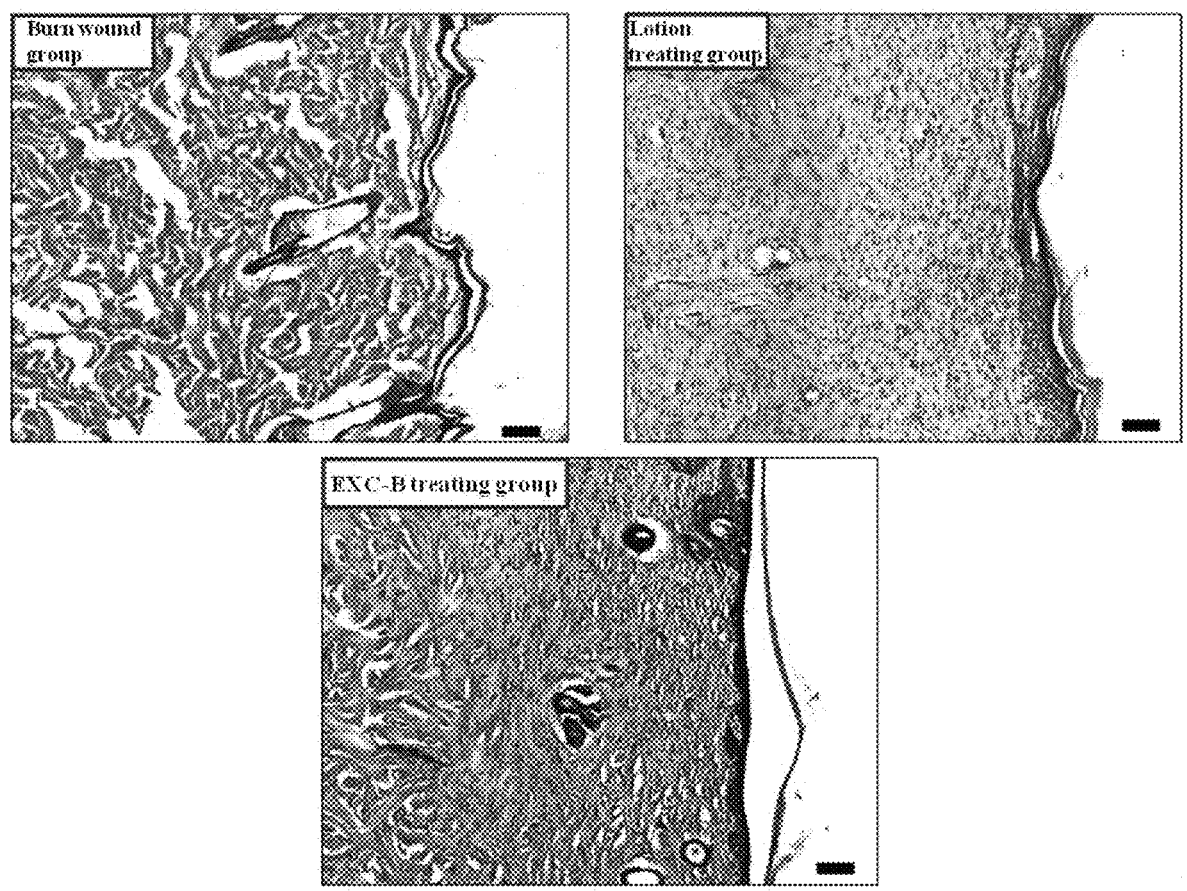
FIG. 5 shows the staining result of a tissue section of the effect of EXC-B on the healing of a burn wound. (A) is the result of the burn wound group (no treatment), (B) is the result of the lotion treating group (administered a normal lotion), and (C) is the result of the EXC-B treating group (treated with a lotion containing EXC-B). Scale bar=200 µm.

FIG. 5 showed the staining result of tissue section of the effect of EXC-B on the healing of a burn wound, in which (A) was a result of the burn wound group (no treatment); (B) was the result of the lotion treating group (administered a normal lotion); and (C) was the result of the EXC-B treating group (treated with a lotion containing a EXC-B). Thickening of the epithelial layer, damages to the dermis and the induction of the infiltration of the neutrophils in both the lotion treating group and the burn wound group could be clearly observed, but tissue changes induced by burn injury in the EXC-B treating group were significantly improved after being treated with the lotion containing EXC-B.

Figure 6:
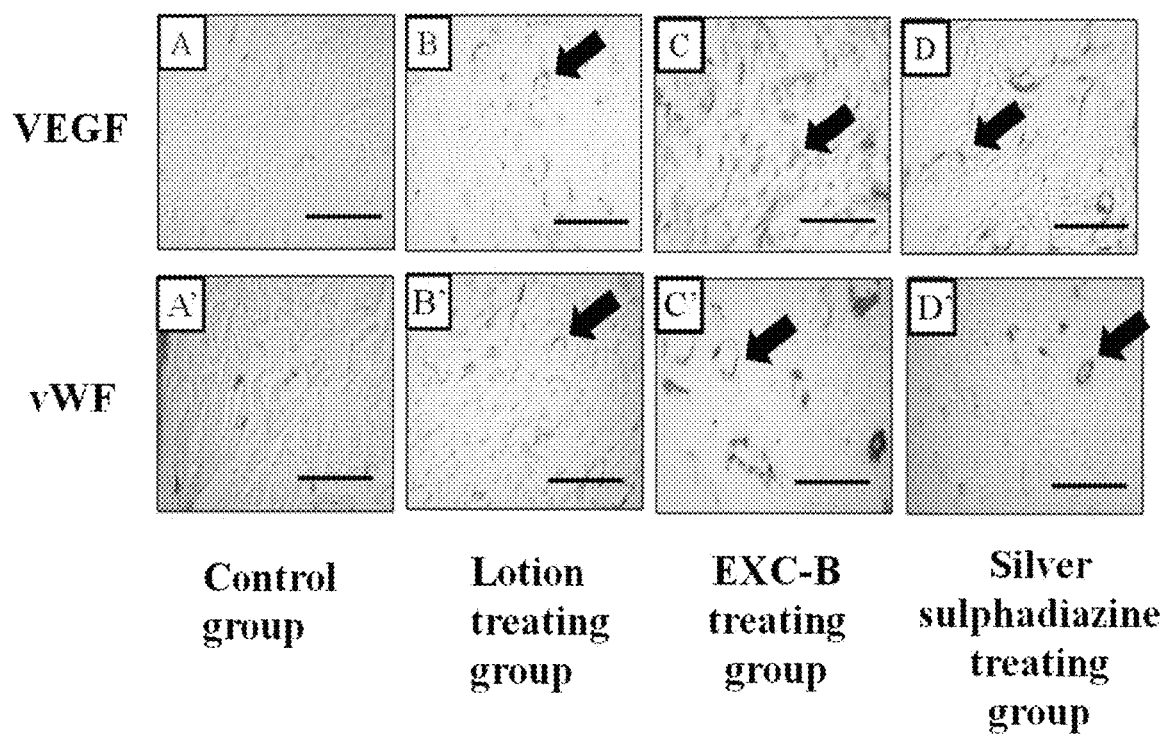
FIG. 6 shows the staining result of the effect of EXC-B on the expression level of the vascular endothelial growth factor (VEGF) and angiogenesis (blood vessels are marked by vWF) in a tissue of a burn wound. (A) and (A') are results of the control group (normal rat), (B) and (B') are results of the lotion treating group (administered a normal lotion), (C) and (C') are results of the EXC-B treating group (treated with a lotion containing EXC-B), and (D) and (D') are results of the silver sulphadiazine treating group (treated with silver sulphadiazine). Scale bar=100 µm.

FIG. 6 showed the staining result of the effect of EXC-B on the expression level of the vascular endothelial growth factor (VEGF) and angiogenesis (blood vessels were marked by vWF) in the tissue of a burn wound, in which (A) and (A') were results of the control group (normal rat); (B) and (B') were results of the lotion treating group (administered a normal lotion); (C) and (C') were results of the EXC-B treating group (treated with a lotion containing EXC-B); and (D) and (D') were results of the silver sulphadiazine treating group (treated with a silver sulphadiazine). A significantly decreased expression level of the VEGF could be clearly observed in the lotion treating group as compared to the control group, but the expression level of the VEGF of the burned tissue was substantially increased after administering the EXC-B and the treating effect of the EXC-B was better than the effect of the silver sulphadiazine. The blood vessels were marked by using the von Willebrand factor (vWF), and it was found that the rate of vascular proliferation in the EXC-B treating group was higher than that of the silver sulphadiazine treating group. The above results showed that the EXC-B treatment could significantly enhance vascular proliferation to shorten the time required for wound healing. Thus, the results clearly indicated that the effective compound EXC-B could accelerate the mechanism of the chronic wound healing by promoting angiogenesis in the wound.

(3) Treating Test of EXC-B on Atopic Eczema

Figure 7:
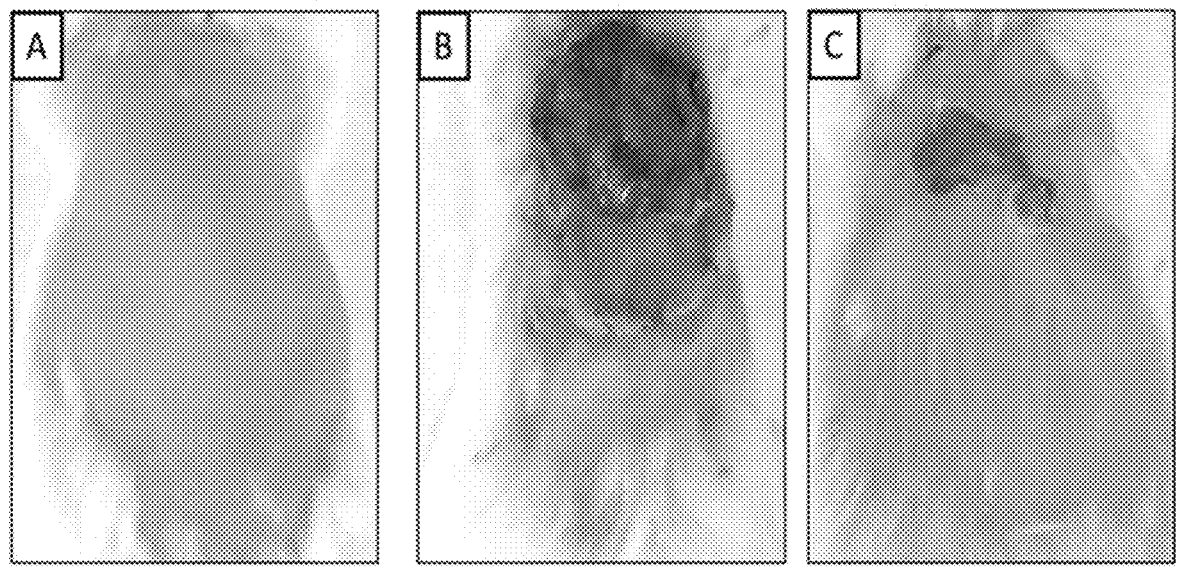
FIG. 7 shows the experimental result of the effect of EXC-B on a skin suffered from atopic eczema. (A) is the result of the control group (normal mice), (B) is the result of the atopic eczema group (administered a normal lotion), and (C) is the result of the EXC-B treating group (treated with 50 µg/0.2 ml of excavatolide B in a lotion).

FIG. 7 showed the experimental result of the effect of EXC-B on a skin suffered from atopic eczema, in which (A) was the result of the control group (normal mice); (B) was the result of the atopic eczema group (administered a normal lotion); and (C) was the result of the EXC-B treating group (treated with 50 μg/0.2 ml of excavatolide B in a lotion). When comparing the atopic eczema group and the control group, it could be observed that there were severe inflammations and scratched wounds caused by repeating itches on the skin of the mice in the atopic eczema group. After the treatment of EXC-B, the condition of the treated skin was significantly better than the skin of the atopic eczema. Thus, the above results showed that EXC-B had very good treating effect for atopic eczema, improved the conditions of inflammations and itches caused by atopic eczema, and no side effects of the clinical treatment were observed, such as skin dryness and albinism.

Figure 8:
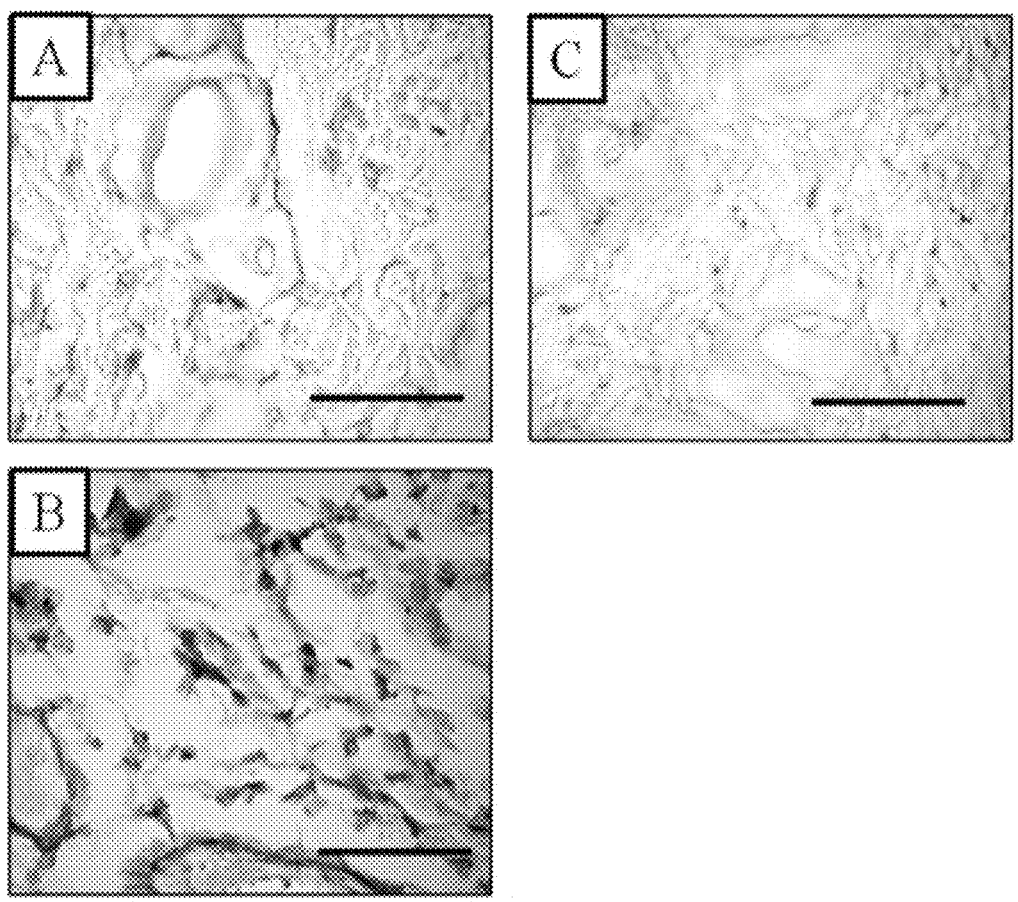
FIG. 8 shows the staining result of the effect of EXC-B on the expression level of the VEGF of a tissue of atopic eczema. (A) is the result of the control group (normal mice), (B) is the result of the atopic eczema group (administered a normal lotion), and (C) is the result of the EXC-B treating group (treated with 50 µg/0.2 ml of excavatolide B in a lotion). Scale bar=100 µm.

FIG. 8 showed the staining result of the effect of EXC-B on the expression level of the VEGF of a tissue of atopic eczema, in which (A) was the result of the control group (normal mice); (B) was the result of atopic eczema group (administered a normal lotion); and (C) was the result of the EXC-B treating group (treated with 50 μg/0.2 ml of excavatolide B in a lotion). In the atopic eczema group, a significant amount of the VEGF was secreted in the tissue of the skin. After EXC-B was administered, the increased expression of the VEGF in the tissue was inhibited. The above results showed that EXC-B could suppress abnormally increased angiogenesis caused by atopic eczema.

Figure 9:
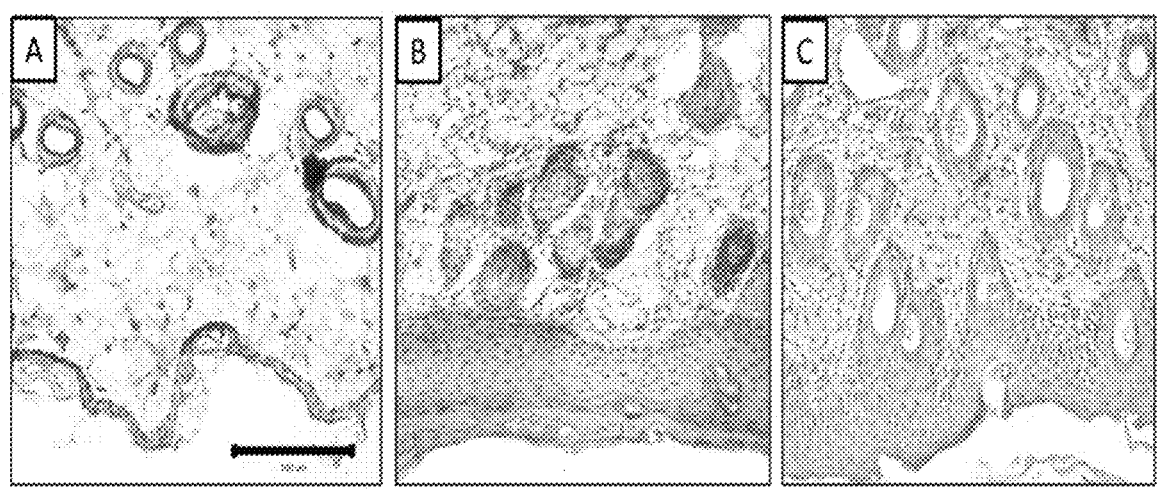
FIG. 9 shows the staining result of the effect of EXC-B on an itchy factor (the marker of the substance P) of atopic eczema. (A) is the result of the control group (normal mice); (B) is the result of the atopic eczema group (administered a normal lotion); and (C) is the result of the EXC-B treating group (treated with 50 µg/0.2 ml of excavatolide B in a lotion). Scale bar=100 µm.

Atopic eczema could cause the skin to secrete various itchy factors (e.g. substance P) which caused the behavior of persistent scratching which would in turn cause continuous damages to layers of the skin. Under above condition, slits in the layer of the skin were generated resulting in a decrease in the moisturizer of the skin, even a wound could be generated. FIG. 9 showed the staining result of the effect of EXC-B on an itchy factor (the marker of the substance P) of atopic eczema, in which (A) was the result of the control group (normal mice); (B) was the result of the atopic eczema group (administered a normal lotion); and (C) was the result of the EXC-B treating group (treated with 50 μg/0.2 ml of excavatolide B in a lotion). It could be observed that there were many itchy factors (the substance P as the marker) in the tissue of the skin in the atopic eczema group as compared to that of the control group and the itchy factors caused repeated scratching. However, the itchy factors (the substance P as the marker) were significantly inhibited after EXC-B was administered. Thus, the above results indicated that EXC-B reduced the repeated itching caused by atopic eczema by reducing the secretion of itchy factors to improve the symptoms of atopic eczema.

Figure 10:
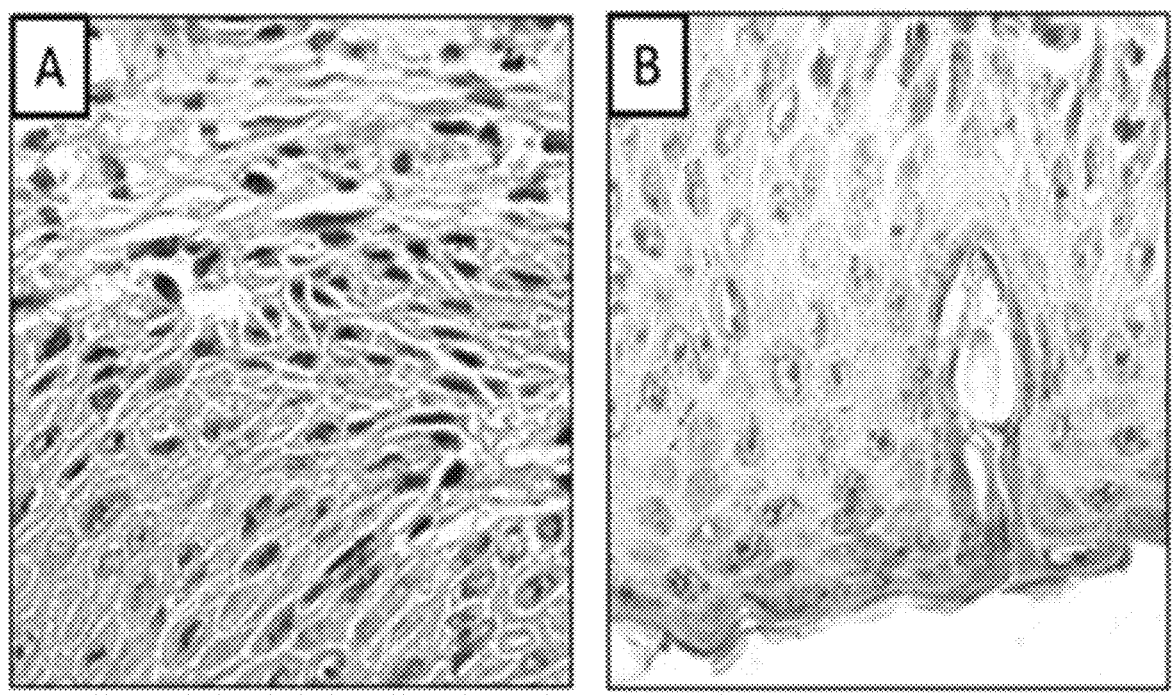
FIG. 10 shows the staining result of the effect of EXC-B on moisturizers of atopic eczema. (A) is the result of the atopic eczema group (administered a normal lotion) and (B) is the result of the EXC-B treating group (treated with 50 µg/0.2 ml of excavatolide B in a lotion).

The abnormal skin barrier also was considered as a primary symptom of atopic eczema. The study indicated that the gene of pro-filaggrin was related to the abnormal skin barrier and was identified as a regulating factor of the skin barrier function. Therefore, the expression level of pro-filaggrin was substantially reduced in atopic eczema. FIG. 10 showed the staining result of the treatment of the moisturizer of atopic eczema by EXC-B, in which (A) was the result of the atopic eczema group (administered a normal lotion); and (B) was the result of the EXC-B treating group (treated with 50 μg/0.2 ml of excavatolide B in a lotion). In the atopic eczema group, it could be observed that atopic eczema could cause a decrease of the regulating factor (the filaggrin as the marker) for skin barrier function, but the decrease of the regulating factor for skin barrier function could be recovered after EXC-B was administered. According to above results, it was demonstrated that EXC-B could improve the abnormal skin barrier function caused by atopic eczema and improve the condition of the skin barrier function to alleviate atopic eczema.

What is claimed is:

1. A method for promoting angiogenesis in a burn wound with vascular atrophy and necrosis in a subject with the burn wound with vascular atrophy and necrosis, which comprises administering an effective amount of composition comprising excavatolide B and a pharmaceutically acceptable carrier to the burn wound with vascular atrophy and necrosis of the subject to promote angiogenesis in the burn wound with vascular atrophy and necrosis by increasing the expression level of vascular endothelial growth factor (VEGF).

2. The method of claim 1, wherein the excavatolide B is extracted from *Briareum excavatum*.

\* \* \* \* \*